(12) United States Patent
Inoue

(10) Patent No.: US 6,716,182 B2
(45) Date of Patent: Apr. 6, 2004

(54) TOOL AND APPLIANCE FOR COLLECTING SLIGHT AMOUNT OF HUMOR

(75) Inventor: Tamotsu Inoue, Fujinomiya (JP)

(73) Assignees: Kabushiki Kaisha Kitazato Supply, Fujinomiya (JP); Masao Jinno, Kawasaki (JP)

( * ) Notice: Subject to any disclaimer, the term of this patent is extended or adjusted under 35 U.S.C. 154(b) by 0 days.

(21) Appl. No.: 10/321,602

(22) Filed: Dec. 18, 2002

(65) Prior Publication Data

US 2003/0088190 A1 May 8, 2003

Related U.S. Application Data

(62) Division of application No. 09/826,818, filed on Apr. 6, 2001, now Pat. No. 6,514,216.

(51) Int. Cl.[7] .................................................. A61D 5/00
(52) U.S. Cl. ....................................................... 600/581
(58) Field of Search ................................. 600/581, 574, 600/575, 569, 570, 572, 576, 573; 436/164, 177, 180; 356/246; 422/72, 918, 922, 58; 73/863.21, 864.02; 604/117, 164.01, 540; 435/287.6

(56) References Cited

U.S. PATENT DOCUMENTS 4,104,025 A  *  8/1978  Retzer ........................ 600/576
4,877,037 A  * 10/1989  Ko et al. .................... 600/569
4,978,504 A    12/1990  Nason
5,078,968 A     1/1992  Nason
5,163,441 A    11/1992  Monthony et al.
5,256,537 A    10/1993  Phillips et al.
5,334,348 A     8/1994  Saito et al.
5,460,781 A    10/1995  Hori et al.
5,665,308 A  *  9/1997  Watanabe .................... 422/58

FOREIGN PATENT DOCUMENTS

JP    7-260777 A    10/1995
JP    7-260778 A    10/1995
JP    2597948 Y2    5/1999

* cited by examiner

Primary Examiner—Max F. Hindenburg
Assistant Examiner—Brian Szmal
(74) Attorney, Agent, or Firm—Burns, Doane, Swecker & Mathis, L.L.P.

(57) ABSTRACT

An appliance for collecting a slight amount of a humor includes a sheath, a humor collection member being slidably inserted into the sheath and having a humor collection part that is formed at a front end thereof and can be cut, and a cylindrical member accommodates a cut piece of the humor collection part which has collected a humor, and a humor collection container installed on the cylindrical member and collecting the humor discharged from the cut piece of the humor collection part by a centrifugal operation with the humor collection container installed on the cylindrical member.

10 Claims, 7 Drawing Sheets

TOOL AND APPLIANCE FOR COLLECTING SLIGHT AMOUNT OF HUMOR

This application is a divisional of application Ser. No. 09/826,818, filed Apr. 6, 2001 now U.S. Pat. No. 6,514,216 B2.

BACKGROUND OF THE INVENTION

The present invention relates to a tool and an appliance for collecting a slight amount of a humor sample to be used in a clinical trial. More particularly, the present invention relates to a tool and an appliance capable of easily and quantitatively collecting a secretory liquid humor sample such as fluid in a uterine cavity, fluid in an oviduct cavity, fluid in a vagina, a cervical mucus, and the like.

Each of the oviduct, the uterus, the uterine cervical canal, and the vagina secretes various growth factors, hormones (Epidermal Growth Factor [EGF], Insulin-like Growth Factor 1 & 2 [IGF 1 & 2], Vascular Endothelial Growth Factor [VEGF], Prolactin [PRL], and the like), and unknown regulatory factors from its epithelium and inner membrane. Owing to the secretion of the regulatory factors, the survival, function, and growth of an ovum, a spermatozoon, a fertilized ovum, an embryo, and a placenta are controlled to allow normal progress of fertilization, embryonic development, implantation, and fetal growth.

The present inventor has found that it is possible to evaluate the oviduct, the uterus, the uterine cervical canal, and the vagina in terms of their abilities of performing the fertilization, the embryonic development, the implantation, and the fetal growth by collecting a slight amount of liquid from the oviduct, the uterus, the uterine cervical canal, and the vagina with the tool and the appliance of the present invention and measuring the concentration of the growth factors, the hormones, and the regulatory factors in the collected humor(fluid). Thereby, the present inventor thinks that the tool and the appliance of the present invention contribute greatly to diagnosis and treatment of various diseases in obstetrics and gynecology such as sterility, habitual abortion, miscarriage, malfunction of the placenta, gestosis, intrauterine growth retardation of the fetus, intrauterine fetal death, abruptio placentae, and the like.

A malignant tumor such as cancer produces and secretes angiogenetic factors such as VEGF and has a host to produce a nutrient blood vessels necessary for growth and metastasis thereof. Many malignant tumors produce and secrete various proteins and hormones (Ca 125, Ca 19-9, Carcinoembryonic antigen [CEA], α-fetoprotein, SLX, SCC, LDH, estradiol, and the like). Therefore, for early diagnosis of cancer in the lumen (cancer of uterus, oviduct, uterine cervical canal, vagina, cavitas nasi, paranasal sinuses, and the like) and their malignancy (metastatic ability), it is useful to collect a slight amount of the fluid (humor) from the lumen (uterus, oviduct, uterine cervical canal, vagina, cavitas nasi, paranasal sinuses, and the like) with the tool and the appliance of the present invention and to measure quantitatively tumor-producing substances contained in the fluid.

A tool for collecting a slight amount of a humor is disclosed in registered Japanese Utility Model No. 2597948.

The collection tool has a collection bar and an outer cylinder. The collection bar has the collection member that is disposed at its distal end and that is formed of a flexible liquid-absorbing material for collecting a humor sample. The outer cylinder has a smaller inner diameter than the outer diameter of the humor collection member and is shorter than the collection bar in its whole length and can accommodate the humor collection member.

However, there is a variation in the amount of a humor to be collected by the humor collection member. Further, it is difficult to take out a small amount of the humor from the humor collection member in examining it, because the humor permeates into the entirety of the big one-piece humor collection member.

It is an object of the present invention to provide a tool and an appliance capable of reliably taking out a humor from a humor collection member, even though the amount of the collected humor is small.

SUMMARY OF THE INVENTION

The object of this invention is to provide a tool for collecting a slight amount of a humor that comprises a sheath, and a humor collection member slidably inserted into said sheath, and wherein said humor collection member has a humor collection part capable of projecting from a front end of said sheath, and said humor collection part can be cut and has a permeation prevention portion which prevents a humor absorbed by said humor collection part from permeating into an entirety of said humor collection part.

Further, the object of this invention is to provide a tool for collecting a slight amount of a humor that comprises, a sheath, and a humor collection member slidably inserted into said sheath, and wherein said humor collection member has a humor collection part capable of projecting from a front end of said sheath; and said humor collection part can be cut and has a plurality of separated humor collection portions.

Further, the object of this invention is to provide an appliance for collecting a slight amount of a humor that comprises a sheath, a humor collection member being slidably inserted into said sheath and having a humor collection part which is formed at a front portion thereof and can be cut and projected from a front end of said sheath, a cylindrical member accommodating a cut piece of said humor collection part which has collected a humor; and a humor collection container installed on said cylindrical member and collecting said humor discharged from said cut piece of said humor collection part by a centrifugal operation.

DETAILED DESCRIPTION OF THE PREFERRED EMBODIMENTS

Figure 1:
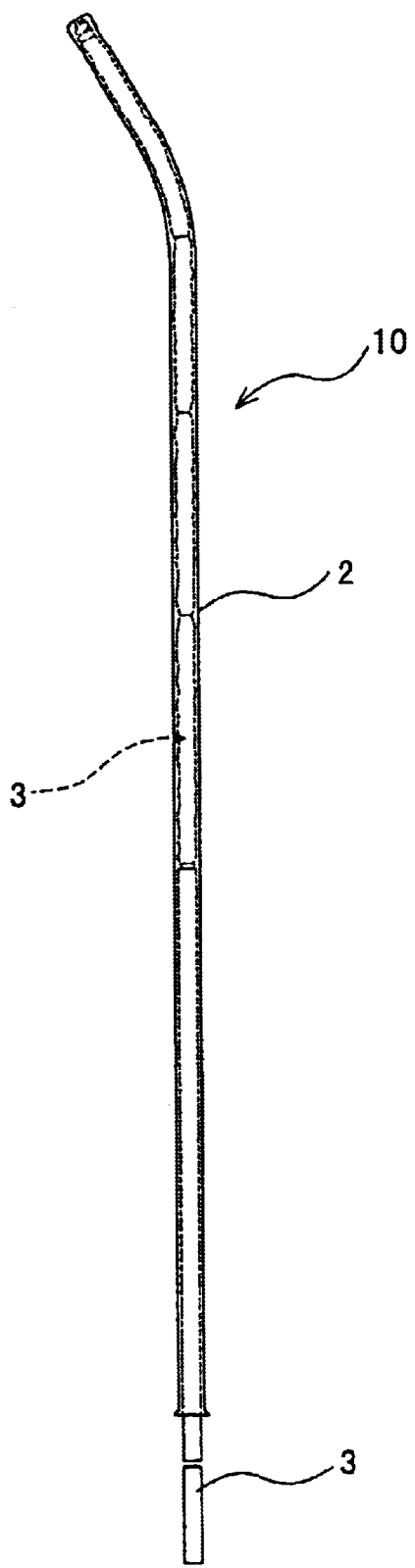
FIG. 1 shows an outlook of an embodiment of a tool for collecting a slight amount of a humor of the present invention.
Figure 2:
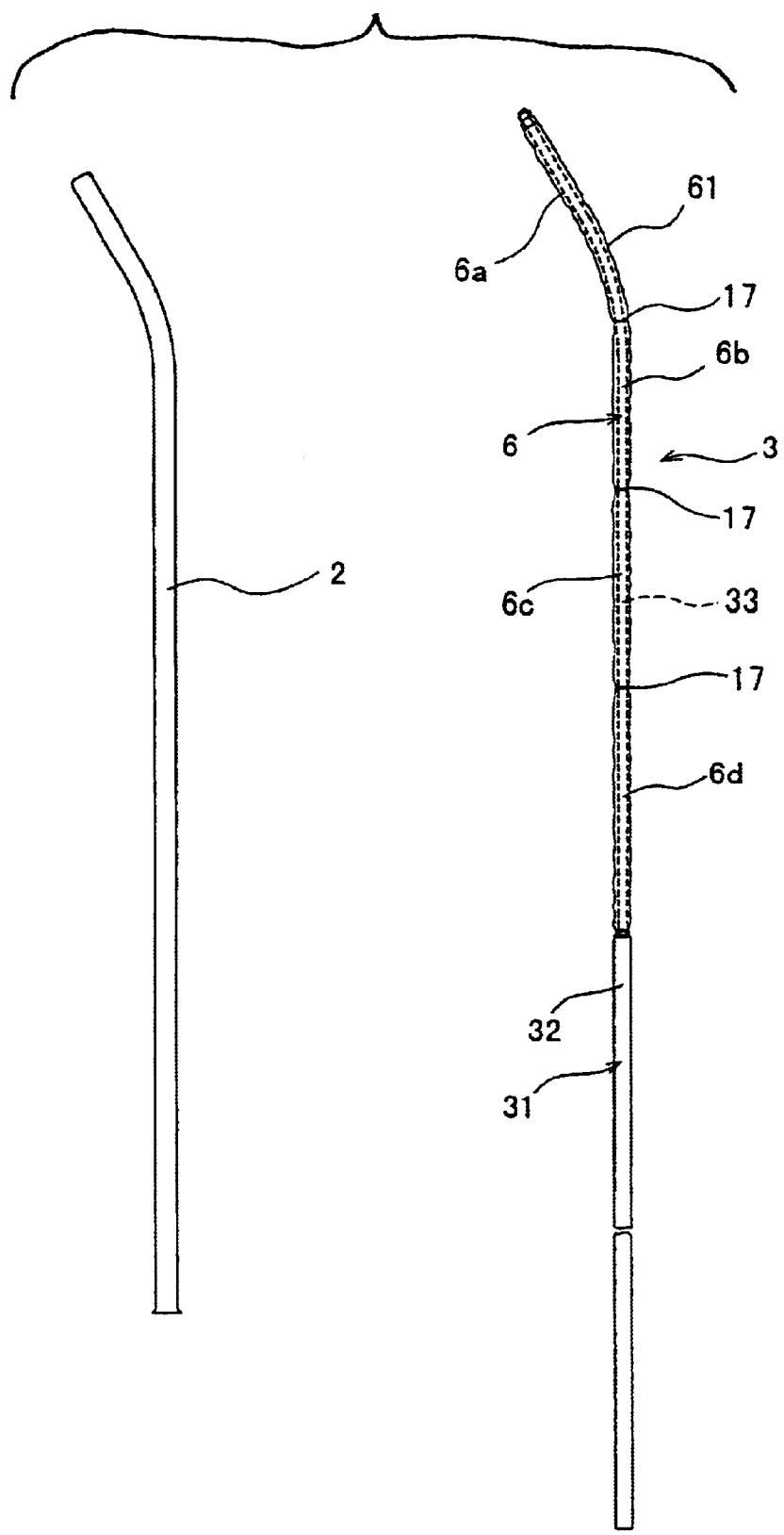
FIG. 2 shows an outlook of constituent members (sheath and humor collection member) of the tool shown in FIG. 1.
Figure 3:
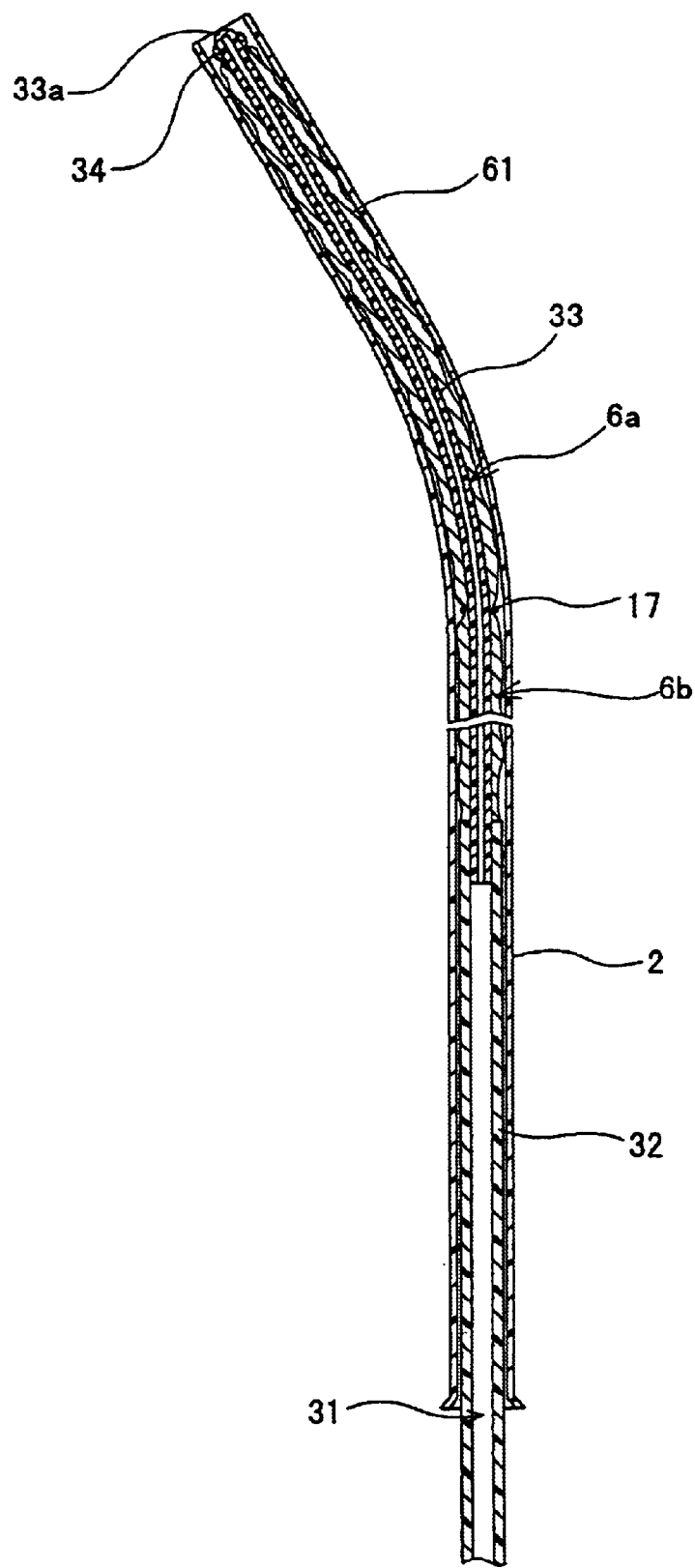
FIG. 3 is enlarged sectional view showing a front portion of the tool shown in FIG. 1.

A preferred embodiment of the tool and the appliance, of the present invention, for collecting a slight amount of a humor will be described in detail below with reference to the accompanied drawings. The tool and the appliance will be hereinafter referred to as merely the tool and the appliance, respectively.

An appliance of the present invention has a sheath 2; a humor collection member 3 being slidably inserted into the sheath 2 and having a humor collection part 6 which is formed at a front end thereof and can be cut; a cylindrical member 4 accommodating a cut piece of the humor collection part 6 which has collected a humor; and a humor collection container 5 installed on the cylindrical member 4 and collecting the humor discharged from the cut piece of the humor collection part 6 by a centrifugal operation.

The tool 10 of the present invention includes the sheath 2 and the humor collection member 3 which is slidably inserted into the sheath 2. The humor collection member 3 has the humor collection part 6 capable of projecting from a front end of the sheath 2. The humor collection part 6 can be cut and has a permeation prevention portion 17 which prevents the humor absorbed by the humor collection part 6 from permeating into the entirety of the humor collection part 6.

The tool 10 includes the sheath 2 and the humor collection member 3 slidably inserted into the sheath 2. The humor collection member 3 has the humor collection part 6 capable of projecting from the front end of the sheath 2. The humor collection part 6 can be cut and has a plurality of separated portions.

The tool 10 will be described more specifically below.

The tool 10 has the sheath 2 and the humor collection member 3.

The sheath 2 functions as a guide tube for guiding the humor collection member 3 into the human body. The sheath 2 is a tube open from its front end to its rear end. In the embodiment, the front portion of the sheath 2 is curved to facilitate the insertion of the tool 10 into a desired portion of the human body. The diameter of the rear portion of the sheath 2 is larger than that of its front portion to facilitate the insertion of the humor collection member 3 into the sheath 2. In other words, the sheath 2 has a tapered rear end portion. The shape of the sheath 2 is not limited to the above-described one, but may be straight.

A material which can retain its shape in a certain extent is preferable for forming the sheath 2. Thus, flexible materials or semirigid materials are preferable. Thus, the following materials are preferable for forming the sheath 2: polyolefin (for example, polyethylene, polypropylene, ethylene-propylene copolymer, ethylene-vinyl acetate copolymer, mixture of polypropylene and polyethylene or polybutene), polyester (polyethylene terephthalate, polybutylene terephthalate), polyamide, vinyl chloride resin (for example, polyvinyl chloride, vinyl chloride-vinyl acetate copolymer, vinyl chloride-ethylene copolymer, vinyl chloride-vinylidene chloride copolymer).

The length of the sheath 2 is different according to a portion of the human body into which it is inserted. For example, in the case where the sheath 2 is inserted into a uterine cavity, its length is favorably 100–300 mm and more favorably 120–250 mm. In the case where the sheath 2 is inserted into an oviduct, its length is favorably 250–450 mm and more favorably 300–400 mm. The outer diameter of the sheath 2 is different according to a portion of the human body into which the sheath 2 is inserted, but is favorably 1–4 mm and more favorably 2.0–3.5 mm.

It is preferable that the front-end surface of the sheath 2 is chamfered, namely, rounded. This shape hardly damages the inner surface of the human body in inserting the sheath 2 and collecting the humor. It is possible to provide the outer surface of the sheath 2 with a marker for checking an insertion depth (length).

The humor collection member 3 has the humor collection part 6 which is formed at its front end portion and can be cut. The humor collection member 3 has the core 31 and a liquid-absorbing portion 61 installed on the outer surface of the front end portion of the core 31. The humor collection part 6 can be cut easily with ordinary cutting means such as scissors, a cutter, and the like. The core 31 has the front end portion 33 that has flexibility and cut easily.

The core 31 has a main portion 32 and a front portion 33 connected to the front end of the main portion 32. The diameter of the front portion 33 is set smaller than that of the main portion 32. The liquid-absorbing portion 61 is mounted on the outer surface of the front portion 33. The humor collection part 6 has the front portion 33 and the liquid-absorbing portion 61 formed on the outer surface of the front portion 33. The humor collection part 6 can be cut without separating the liquid-absorbing portion 61 and the front portion 33 of the core 31 from each other, with the liquid-absorbing portion 61 held on the outer surface of the front portion 33 of the core 31. A one-piece different-diameter linear material or a one-piece different-diameter tube having a small-diameter portion at its front side may be used as the core 31.

Figure 4:
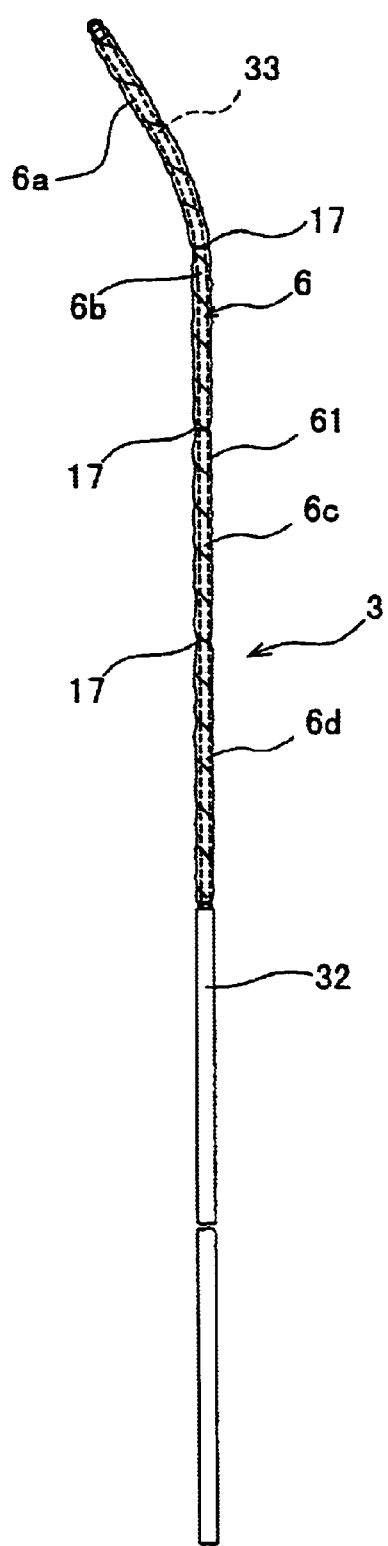
FIG. 4 shows an outlook of a humor collection member to be used in another embodiment of the tool of the present invention.
Figure 5:
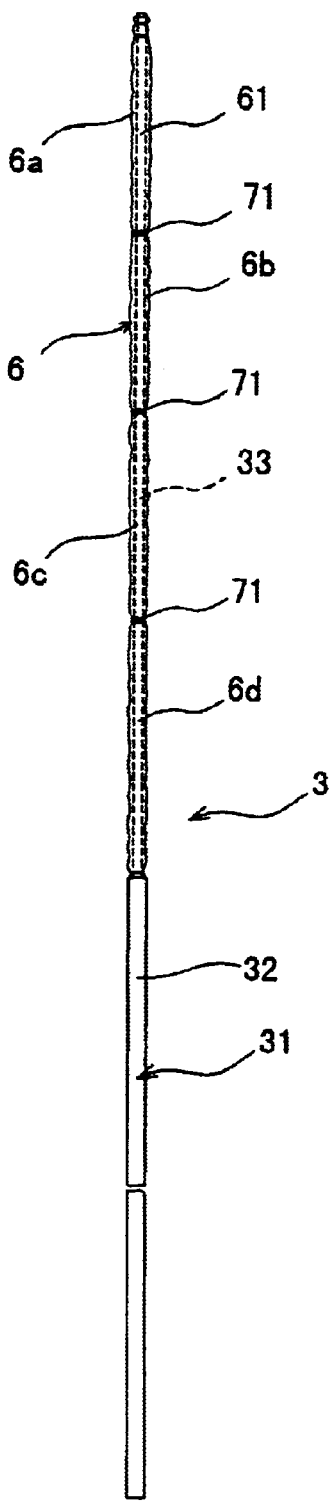
FIG. 5 shows an outlook of a humor collection member to be used in another embodiment of the tool of the present invention.
Figure 6:
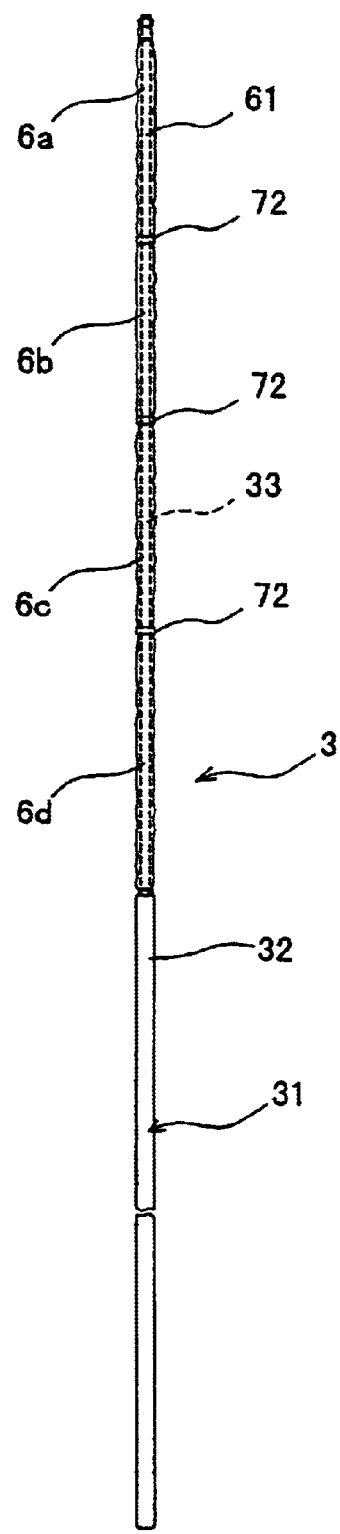
FIG. 6 shows an outlook of a humor collection member to be used in another embodiment of the tool of the present invention.
Figure 7:
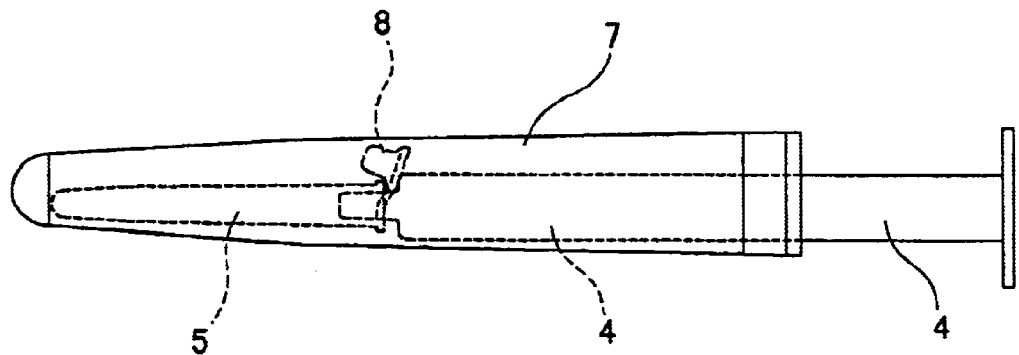
FIG. 7 shows an outlook of a state in which a cylindrical member is inserted into a container for centrifugal operation to be used for of an appliance of embodiment of the present invention for collecting a slight amount of a humor.
Figure 8:
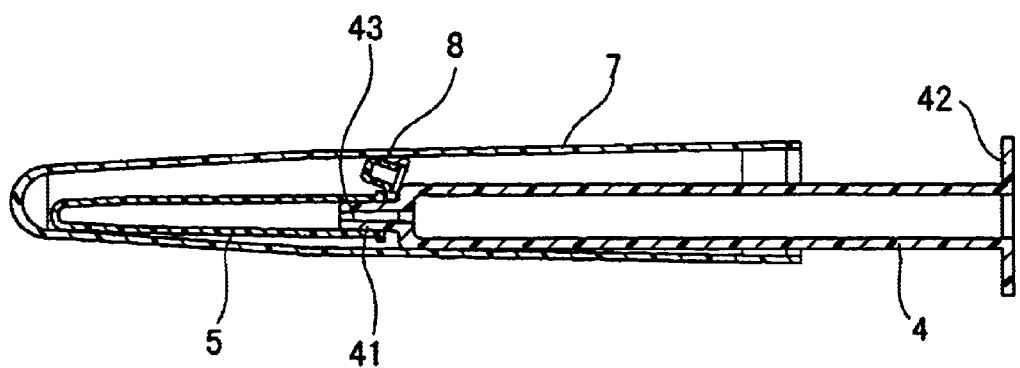
FIG. 8 is a sectional view of the cylindrical member shown in FIG. 7.

The liquid-absorbing portion 61 contacts a humor sample collection portion in the interior or exterior of the human body and absorbs (liquid)/holds the liquid humor sample. The liquid-absorbing portion 61 is formed of a liquid-absorbing material having a certain degree of flexibility. In the embodiment, the liquid-absorbing portion 61 has a shape of a long and narrow belt. More specifically, the core 31 is enclosed with the liquid-absorbing portion 61 by sandwiching the outer surface of the core 31 (front portion 33) between two belt-shaped liquid-absorbing portions 61. The liquid-absorbing portion 61 covers a part of or all of the front end portion 33 of the core 31. The belt-shaped liquid-absorbing portion 61 is bound at a plurality of portions with thread. The portion bound with the thread constitutes the permeation prevention portion 17 for preventing the humor absorbed by the humor collection part 6 from permeating into the entirety of the humor collection part 6. In other words, the humor collection part 6 has a plurality of separated humor collection portions 6a, 6b, 6c, and 6d. It is necessary that the humor collection part 6 has at least two separable portions. The humor collection part 6 has favorably 2–10 separated portions and more favorably 3–7 separated portions. In the embodiment, the liquid-absorbing portion 61 is bound at five portions including the front and rear ends thereof. Thus, the humor collection part 6 has four separable portions. In another embodiment, as shown in FIG. 4, the belt-shaped liquid-absorbing portion 61 may be wound spirally on the core 31 and bound at a plurality of portions with thread, as described above to form the permeation prevention portions 17. The portion bound with the thread constitutes the permeation prevention portion 17 for preventing the humor absorbed by the humor collection part 6 from permeating into the entirety of the humor collection part 6. The permeation prevention portion 17 is not necessarily formed with the thread. For example, as shown in FIGS. 5 and 6, the permeation prevention portion 17 may be formed with an annular partitioning portion. In the permeation prevention portion 17 shown in FIG. 5, an annular partitioning portion 71 fixes the liquid-absorbing portion 61 annularly partly to the core 31 with resin or an adhesive agent so that a fixed portion prevents the permeation of an absorbed liquid into the entirety of the humor collection part 6. The permeation prevention portion 17 is not necessarily formed with the thread. For example, as shown in FIG. 6, the permeation prevention portion 17 may be formed with a plurality of partitioning portions each consisting of an annular rib 72 preventing permeation of a liquid into the entirety of the humor collection part 6.

The liquid-absorbing portion 61 is not necessarily belt-shaped. For example, the liquid-absorbing portion 61 may be cylindrical or may be wound directly on the front portion 33 like a swab. In the humor collection member 3 shown in FIG. 6, the core 31 has a plurality of annular partitioning portions. The liquid-absorbing portion 61 is disposed between adjacent annular partitioning portions.

The front portion of the humor collection member 3 is curved to facilitate its insertion into the desired portion of the human body. A front end 33a of the core 31 is closed. It is preferable that the front-end surface of the humor collection member 3 is curved. More specifically, the front end of the humor collection part 6 is formed of the core 31, and the surface of the front end of the core 31 is rounded. The tip end of the core is closed and rounded. The rounded front-end of the core 31 can be shaped by melting the front end thereof. The side surface of the front end of the core 31 is also rounded. The rounded side surface of the front end of the core 31 is formed by fixing a bead-shaped spherical body 34 penetrating the front end of the core 31 to the front end of the core 31. In this embodiment, the core has a bead having a smaller diameter than an inner diameter of the sheath and fixed to the front tip end of the core 31.

It is preferable to form the core (front portion 33 and main portion 32) 31 of liquid-unabsorbent flexible materials. Thus, the following materials are preferable for forming the core 31: polyolefin (for example, polyethylene, polypropylene, ethylene-propylene copolymer, ethylene-vinyl acetate copolymer, mixture of polypropylene and polyethylene or polybutene), olefin elastomer (polyethylene elastomer, polypropylene elastomer), polyester (polyethylene terephthalate, polybutylene terephthalate), polyamide, amide elastomer (polyamide elastomer), soft vinyl chloride, styrene elastomer (for example, styrene-butadiene-styrene copolymer, styrene-isoprene-styrene copolymer, styrene-ethylene butylene-styrene copolymer), polyurethane, urethane elastomer, silicone rubber, synthetic rubber such as butadiene rubber, and natural rubber such as latex rubber.

Preferably, the main portion 32 of the core 31 is tubular but may be solid. Preferably, the front portion 33 is also tubular but may be solid.

The length of the humor collection member 3 is different according to a desired portion of the human body into which the humor collection member 3 is inserted, but is longer than the sheath 2 by favorably 30–200 mm and more favorably by 50–150 mm. More specifically, in the case where the humor collection member 3 is inserted into the uterine cavity, its length is favorably 200–450 mm and more favorably 250–400 mm. In the case where the humor collection member 3 is inserted into the oviduct, its length of is favorably 300–550 mm and more favorably 350–500 mm. The outer diameter of the humor collection member 3 (humor collection part 6 and main portion 32) is different according to a portion of the human body into which the humor collection member 3 is inserted, but is favorably 1–4 mm and more favorably 1.5–3.0 mm.

It is preferable that the outer diameter of the humor collection member 3 is equal to or smaller than the inner diameter of the sheath 2 to facilitate the operation of the humor collection member 3. Even when the humor collection part 6 of the humor collection member 3 absorbs a humor and swells, it is easy to perform an operation of accommodating the humor collection member 3 in the sheath 2. More specifically, the outer diameter of the humor collection member 3 is favorably 1–4 mm and more favorably 1.5–3.0 mm.

The length of the humor collection part 6 (length of the front portion 33) is different according to a desired portion of the human body into which the humor collection member 3 is inserted. More specifically, in the case where the humor collection member 3 is inserted into the uterine cavity, the length of the humor collection part 6 is favorably 50–150 mm and more favorably 75–130 mm. In the case where the appliance is inserted into the oviduct or the uterine cavity, the length of the humor collection part 6 is favorably 50–100 mm and more favorably 30–60 mm. The outer diameter of the front portion 33 is equal to or smaller than the inner diameter of the sheath 2. More specifically, the outer diameter of the humor collection member 3 is favorably 1–4 mm and more favorably 1.5–3.0 mm.

Fibrous and porous materials can be preferably utilized to form the liquid-absorbing portion 61. More specifically, as the material for the liquid-absorbing portion 61, it is possible to use woven cloth, nonwoven cloth, and absorbent cotton consisting of cotton, chemical fiber or a mixture of the cotton and the chemical fiber; a porous polymer such as sponge, resinous foam; and paper. The mode of the liquid-absorbing portion 61 is not limited to the above-described modes, but any kind of modes can be used, so long as they do not prevent smooth cutting of the humor collection part 6. For example, the liquid-absorbing portion 61 may be cylindrical, spherical or cocoon-shaped, with the front end of the core 31 placed on the center.

The appliance of the present invention has the sheath 2; the humor collection member 3 having the humor collection part 6 which is formed at a front end thereof and can be cut; the cylindrical member 4 accommodating a cut piece of the humor collection part 6 which has collected a humor; and the humor collection container 5 installed on the cylindrical member 4 and collecting the humor discharged from the cut piece of the humor collection part 6 by a centrifugal operation.

The above-described materials can be preferably used for the sheath 2 and the humor collection member 3. The humor collection member 3 is not limited to the above-described one. Provided that the humor collection member 3 has the humor collection part 6 which is formed at its front end and can be cut, it is possible to use the humor collection member not having the permeation prevention portion 17 for preventing the humor absorbed by the humor collection part 6 from permeating into the entirety of the humor collection part 6 or the humor collection member 3 in which the humor collection part 6 does not have a plurality of separable portions.

The cylindrical member 4 serves as the means for accommodating the cut piece of the humor collection part 6 which has collected the humor.

The cylindrical member 4 has a small-diameter portion 41 whose front end is open at its front portion. The cylindrical member 4 has a flange 42 at its rear end. The inner diameter of the front portion of the cylindrical member 4, namely, the inner diameter of the small-diameter portion 41 is set smaller than the outer diameter of the cut piece of the humor collection part 6. Thereby, the cylindrical member 4 prevents the movement of the cut piece of the humor collection part 6 to the front end of the humor collection container 5. To securely prevent the movement of the cut piece, it is preferable that the inner diameter of the front portion of the cylindrical member 4 is smaller the outer diameter of the core 31 of the cut piece. The cylindrical member 4 has a humor flowing portion 43 having a smaller diameter than the outer diameter of the cut piece of the humor collection part 6.

It is preferable that the length of the cylindrical member 4 is 40–150 mm and that its inner diameter is 3–10 mm. It is preferable that the length of front portion (small-diameter portion 41) of the cylindrical member 4 is 3–20 mm and that the inner diameter of the front portion thereof is 0.5–3 mm.

The humor collection container 5 is installed on the cylindrical member 4 and serves as the means for collecting the humor discharged from the cut piece of the humor collection part 6 by a centrifugal operation.

The humor collection container 5 is cylindrical and open at its rear end and closed at its front end. The rear portion of the humor collection container 5 can be installed substantially liquid-tightly on the front portion of the cylindrical member 4. The front side of the humor collection container 5 tapers off to its front end. It is preferable that the humor collection container 5 has a cap 8, for sealing the rear end thereof, which opens after the humor collection container 5 collects the humor. In the embodiment, the humor collection container 5 has the cap 8 connected thereto through a connection portion.

It is preferable that the length of the humor collection container 5 is 10–100 mm and that its inner diameter is 2–8 mm.

The humor collection container 5 may accommodate a serum separation agent. The serum separation agent has a specific gravity intermediate between that of a serum or that of a blood plasma component and that of a blood clot or that of a blood cell component. The serum separation agent has the specific gravity intermediate between the specific gravity 1.03–1.08 of the serum component at 25° C. and that of the blood clot component. Preferably, the serum separation agent is thixotropic and gelled. To form the serum separation agent having such properties, silicone oil, chlorinated polybutene, acrylic polymer, a copolymer of sebacic acid and diol, or an α-olefin diester maleate copolymer is prepared to form a main component. Inorganic powder such as silica or clay and organic gelatinizing agent are added to the main component to hold the specific gravity, viscosity or configuration of the resulting serum separation agent. As examples of the serum separation agent, it is possible to use thixotropic gelled separation agent ["escollect" produced by Sekisui Kagaku Corp., specific gravity: 1.05, viscosity: 150,000 cp (25° C.)] obtained by kneading cyclopentadiene resin, dibenzylidiene sorbitol, silica, and phthalic acid (2-ethylhexyl).

It is preferable that the appliance has a container 7, for centrifugal operation, accommodating the cylindrical member 4, with the humor collection container 5 mounted on the cylindrical member 4. The container 7 for centrifugal operation facilitates a centrifugal separation operation and prevents the cylindrical member 4 and the humor collection container 5 from separating from each other during the centrifugal separation operation.

Figure 9:
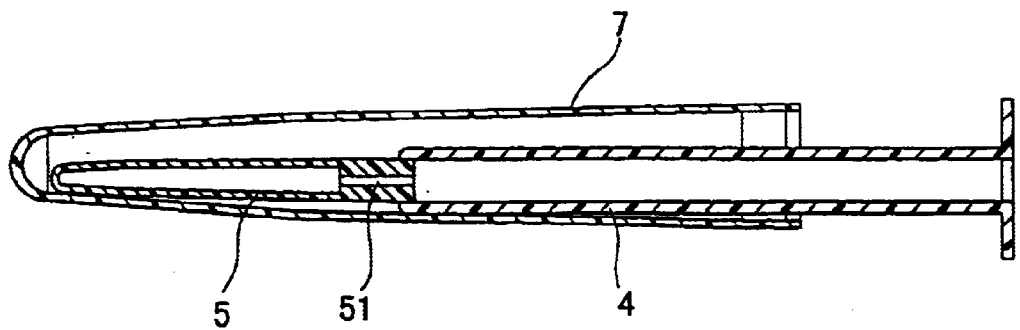
FIG. 9 is a sectional view of another cylindrical member is inserted into a container for centrifugal operation to be used for of an appliance, of another embodiment of the present invention, for collecting a slight amount of a humor.

The cylindrical member 4 and the humor collection container 5 do not necessarily have the above-described construction. For example, as shown in FIG. 9, instead of providing the cylindrical member 4 with the small-diameter portion, a small-diameter portion is formed at the rear end of the humor collection container 5 to constitute a movement prevention portion for preventing movement of the cut piece of the humor collection part 6 to the front end of the humor collection container 5. In this case, the humor collection container 5 has a humor flowing portion 51 having a smaller diameter than the outer diameter of the cut piece of the humor collection part. In this case, the appliance is not necessarily provided with the container 7 for centrifugal operation.

The container 7 for centrifugal operation is cylindrical and capable of accommodating more than half of the cylindrical member 4, with the humor collection container 5 mounted on the cylindrical member 4 in a direction from the front end of the cylindrical member 4 (in other words, in a direction from the humor collection container 5). The container 7, for centrifugal operation, of the embodiment is cylindrical and open at its rear end and closed at its front end. The container 7 for centrifugal operation is long enough to accommodate ½–¼ (entirety) of the whole length of the cylindrical member 4, with the humor collection container 5 mounted thereon. Considering that the cylindrical member 4 is taken out from the container 7 for centrifugal operation, with the humor collection container 5 mounted thereon, it is preferable that the container 7 for centrifugal operation accommodates the cylindrical member 4 in such a way that the rear portion of the cylindrical member 4 is exposed, with the humor collection container 5 mounted thereon.

It is preferable that the length of the container 7 for centrifugal operation is 40–150 mm and that its inner diameter is 5–20 mm. It is preferable to form the cylindrical member 4, the humor collection container 5, and the container 7, for centrifugal operation, of a transparent material or a semitransparent material. The following resins can be used to form the cylindrical member 4, the humor collection container 5, and the container 7 for centrifugal operation: polypropylene, polyethylene, polystyrene, polyamide, polycarbonate, polyvinyl chloride, poly-(4-methylpentene-1), acrylic resin, acrylonitrile-butadiene-styrene copolymer, and polyester such as polyethylene terephthalate. Polypropylene is most favorable of these resins because polypropylene is easy to form and has heat resistance.

The method of using the tool and the appliance of the present invention will be described below.

Initially, as shown in FIG. 1, the sheath 2 is inserted into a desired humor collection portion inside the human body, with the sheath 2 accommodating the humor collection part 6 of the humor collection member 3. Thereafter, the humor collection member 3 is pressed to expose the humor collection part 6 from the front end of the sheath 2. In this state, the humor collection part 6 absorbs the humor. After the humor collection part 6 of the humor collection member 3 is accommodated again in the sheath 2, the sheath 2 and the humor collection member 3 are removed from the desired portion of the human body.

Because after the humor collection member 3 collects the humor, it can be removed from the human body, with the sheath 2 accommodating the humor collection member 3, it is possible to prevent the humor from being contaminated with humors other than the humor to be collected.

After the humor collection member 3 is removed from the sheath 2, the humor collection part 6 is cut with scissors to prepare one or a plurality of cut pieces of the humor collection part 6. One or a plurality of the cut pieces of the humor collection part 6 are put into the cylindrical member 4 from its rear end, with the humor collection container 5 mounted at the front end of the cylindrical member 4. Then, the cylindrical member 4 is inserted into the container 7 for centrifugal operation, with the humor collection container 5 mounted on the cylindrical member 4. Then, the container 7 for centrifugal operation is put into a centrifugal machine to centrifuge the humor. Thereby, the humor absorbed by the cut piece of the humor collection part 6 moves to the humor collection container 5 and is collected. The cylindrical member 4 on which the humor collection container 5 has been mounted is taken out from the container 7 for centrifugal operation. Then, the humor collection container 5 is removed from the cylindrical member 4. As the final step of the humor collection operation, the open portion of the humor collection container 5 is sealed with the cap 8.

The process of collecting the humor of the uterine cavity with the tool and the appliance of the present invention will be described below.

After a vaginal speculum is inserted into the vagina and the vagina is sterilized, a disinfectant is washed away from the vagina sufficiently with a physiologic saline. After the physiologic saline is eliminated completely with gauze, the sheath 2 is inserted into a position a little inward from the internal orifice through the uterine cervical canal, with the sheath 2 accommodating the humor collection part 6 of the humor collection member 3. When the sheath 2 passes the internal orifice of the uterus, the insertion of the sheath 2 is stopped. Then, only the humor collection member 3 is inserted into the uterine cavity by about 10 cm to put the entire humor collection part 6 of the humor collection member 3 into the uterine cavity. The humor collection member 3 is left stationary for one minute so that the humor collection part 6 absorbs the humor of the uterine cavity. After the humor collection member 3 is completely returned into the sheath 2, the tool is removed from the uterine cervical canal. After the humor collection member 3 is pressed out from the sheath 2, the front end of the humor collection member 3 is cut off with scissors. While the humor collection part 6 is being inserted into the cylindrical member 4, with the humor collection container 5 mounted at its front end, the humor collection part 6 is appropriately cut. Then, the cut piece is accommodated in the cylindrical member 4. To prevent vaporization of the humor, the rear end of the cylindrical member 4 is sealed with an adhesive tape or a cap. The cylindrical member 4 is inserted into the container 7 for centrifugal operation to centrifuge the humor by the centrifugal machine, with the centrifugal machine accommodating the container 7 for centrifugal operation. Normally, the centrifugal machine is driven at 3500 rpm for 15 minutes. Owing to the centrifugation, a blood cell component deposits in the lower layer of the humor collection container 5, and a liquid component of the uterine cavity is present in the upper layer thereof. The liquid component of the uterine cavity present in the upper layer thereof is aspirated with a micro-pipette and put in another humor collection container to refrigerate it or preserve it in a frozen state until it is measured. If necessary, the open portion of the humor collection container 5 is sealed with a cap. If the serum separation agent is accommodated in the humor collection container 5, it is possible to prevent the liquid component of the uterine cavity present in the upper layer of the humor collection container 5 from being contaminated with a hemolytic blood cell component after the humor is centrifuged. Therefore, the examination can be accomplished securely.

A slight amount of a humor of the oviduct and humors of other lumens are collected in a method similar to the above-described method of collecting the liquid component of the uterine cavity, except that a laparoscope and a different technique are used to reach the tool and the appliance to each lumen.

The tool of the present invention includes the sheath and the humor collection member which is slidably inserted into the sheath. The humor collection member has the humor collection part capable of projecting from a front end of the sheath. The humor collection part can be cut and has a permeation prevention portion which prevents the humor absorbed by the humor collection part from permeating into the entirety of the humor collection part.

The tool of the present invention includes the sheath and the humor collection member slidably inserted into the sheath. The humor collection member has the humor collection part capable of projecting from the front end of the sheath. The humor collection part can be cut and has a plurality of separable portions.

In this construction, even though the amount of the collected humor is small, the permeation of the humor into the entire humor collection part is prevented. Thus, it is possible to take out the humor from the humor collection member by a centrifugal operation to be performed afterward. Further, because the humor collection part can be cut, it is easy to prepare a cut piece, of the humor collection part, required in performing the centrifugal operation.

The appliance of the present invention has a sheath; a humor collection member being slidably inserted into the sheath and having a humor collection part which is formed at a front end thereof and can be cut; a cylindrical member accommodating a cut piece of the humor collection part which has collected a humor; and a humor collection container installed on the cylindrical member and collecting the humor discharged from the cut piece of the humor collection part by a centrifugal operation.

Accordingly, it is easy to take out the humor collected by the humor collection part from the humor collection member by performing the centrifugal operation. Further, because the humor collection part can be cut, it is easy to prepare the cut piece, of the humor collection part, required in performing the centrifugal operation.

What is claimed is:
1. An appliance for collecting a slight amount of a humor comprising:
   a sheath;
   a humor collection member being slidably inserted into said sheath and having a humor collection part which is formed at a front portion thereof and can be cut and projected from a front end of said sheath;
   a cylindrical member accommodating a cut piece of said humor collection part which has collected a humor; and
   a humor collection container installed on said cylindrical member and collecting said humor discharged from said cut piece of said humor collection part by a centrifugal operation.

2. An appliance according to claim 1, wherein said appliance has a container for centrifugal operation accommodating said cylindrical member, with said humor collection container mounted on said cylindrical member.

3. An appliance according to claim 1, wherein said cylindrical member or said humor collection container has a movement prevention portion for preventing movement of said cut piece of said humor collection part to a front end of said humor collection container.

4. An appliance according to claim 1, wherein said cylindrical member or said humor collection container has a humor flowing portion having a smaller diameter than an outer diameter of said cut piece of said humor collection part.

5. An appliance according to claim 1, wherein said humor collection part has a permeation prevention portion preventing an absorbed humor from permeating into an entirety of said humor collection part.

6. An appliance according to claim 1, wherein said humor collection part has a plurality of separated humor collection portions.

7. An appliance according to claim 1, wherein said humor collection member includes a core and a liquid-absorbing portion mounted on an outer surface of a front portion of said core.

8. An appliance according to claim 1, wherein a front end of said humor collection part is formed of said core and a front-end surface of said core is closed and rounded.

9. An appliance according to claim 1, wherein a front portion of said sheath is curved.

10. An appliance according to claim 1, wherein said humor collection member includes a core having a front end portion having flexibility and cut easily and a liquid-absorbing portion covering a part of or all of the front end portion of the core and bound at a plurality of portions with thread, and said humor collection part is formed by the front end portion of the core and the liquid-absorbing portion.

* * * * *

UNITED STATES PATENT AND TRADEMARK OFFICE
CERTIFICATE OF CORRECTION

PATENT NO. : 6,716,182 B2
DATED : April 6, 2004
INVENTOR(S) : Tamotsu Inoue

It is certified that error appears in the above-identified patent and that said Letters Patent is hereby corrected as shown below:

<u>Title page,</u>
Insert Item: -- [30]   Foreign Application Priority Data
           April 7, 2000    (JP)     2000-107157 --.

Signed and Sealed this

Sixteenth Day of May, 2006

JON W. DUDAS
*Director of the United States Patent and Trademark Office*